United States Patent [19]

Duminy-Kovarik

[11] Patent Number: 4,701,275

[45] Date of Patent: Oct. 20, 1987

[54] TESTING SYSTEM

[75] Inventor: Isabelle Y. Duminy-Kovarik, Malta, Ill.

[73] Assignee: Circle Chemical Company, Inc., Hinckley, Ill.

[21] Appl. No.: 908,251

[22] Filed: Sep. 17, 1986

[51] Int. Cl.$^4$ .................. H01L 1/28; G01N 27/82; C09K 1/02

[52] U.S. Cl. .................. 252/62.52; 324/216; 324/238; 436/806

[58] Field of Search ..................... 252/62.52

[56] References Cited

U.S. PATENT DOCUMENTS

| | | | |
|---|---|---|---|
| 2,461,494 | 2/1949 | de Forest | 175/183 |
| 2,868,734 | 1/1959 | De Castro | 252/358 |
| 2,936,287 | 5/1960 | Kazenas | 252/62.52 |
| 3,214,378 | 10/1965 | Hanneman | 252/62.5 |
| 3,499,148 | 3/1970 | Nestler et al. | 252/62.52 |
| 3,597,356 | 8/1971 | Diperstein et al. | 252/62.52 |
| 3,786,346 | 1/1974 | Lorenzi | 324/38 |
| 3,990,981 | 11/1976 | Kovac et al. | 252/62.52 |
| 4,094,804 | 6/1978 | Shimoiizaka | 252/62.52 |

FOREIGN PATENT DOCUMENTS 585294  2/1947  United Kingdom ............. 252/62.52

Primary Examiner—Arthur P. Demers
Attorney, Agent, or Firm—Mathew R. P. Perrone, Jr.

[57] ABSTRACT

An aqueous system for testing magnetizable articles is provided by a water based slurry of magnetic particles including a corrosion inhibitor, surface tension adjusting agent, an antifoam agent, a viscosity adjustment element, and a buffering element to assist in the corrosion resistance.

20 Claims, No Drawings

TESTING SYSTEM

BACKGROUND OF THE INVENTION

This invention relates to a testing system and more particularly to an aqueous system for testing magnetizable articles.

It is always desirable to test an article before it is placed in use. Such testing can assist in determination of flaws not readily visible to the human eye. It is highly critical to determine the flaws. These otherwise invisible flaws can result in major weaknesses and a failure in the article with disasterous results. Thus, it is desirous to test articles.

One way to test an article is to completely destroy it and examine the resulting fractured pieces. This method is, however, destructive and denies the use of the part after substantial work is done to make the part. This testing is also based on statistical foundations. This method can only be used with a group of the articles, wherein one article from that group is selected at random for testing.

If the selected article passes the test, from a statistical standpoint, the odds as to whether the other articles are safe can be determined. Clearly the random selection of a part or an article for testing leaves too much to chance. There is no test of all the articles, and no positive indication of the safety of all the articles.

Furthermore, the destructive nature of the test renders the article unsuitable for use. Destructive testing is, therefore, costly and wasteful. Cost and waste are clearly factors to be reduced in the interest of improving production.

To avoid the problems caused by destructive testing, various methods are known. Typical methods of testing can be used depending on the nature of the article. For example, if an article is magnetizable, a certain test may be used to determine flaws in the article. The article—usually of steel or iron—is coated with a liquid bath containing magnetic inspection particles. At a suitable point during the inspection process, the article is magnetized. The particles are then attracted to variations in the flux field of the magnetized article. The variations are caused by the defects in the article.

In theory and in actual practice, the slurry containing the magnetic inspection particles coats the surface of the article being tested. The particles are then attracted to the defects in the article in the same manner as magnetic items are attracted to the poles of a magnet. The build-up of particles at the flaws caused by this magnetic force make the flaws clearly evident. In this fashion, flaws, otherwise invisible to the human eye, can be detected when placed under a proper light. This procedure is generally referred to as the wet method of magnetic particle inspection.

There are many key factors in applying the magnetic inspection particles to the article to be tested. The liquid medium for carrying the particles to the surface of the article to be tested must have appropriate viscosity, which allows for complete wetting of the surface of the article without inhibiting particle migration. This works in combination with the appropriate surface tension and corrosion inhibition level to allow for proper particle suspension and dispersion in the slurry—as well as providing the required protection from corrosion. If these factors are met for the liquid medium, better migration of the particles to the defect during and following the magnetizing process on the article is achieved.

The value of using a non-fluorescent medium to eliminate background fluorescence is considered, due to its importance to most applications. An aqueous medium meeting this requirement of eliminating background fluorescence can then be used with fluorescent magnetic inspection particles—provided the other criteria for magnetic particle inspection systems can be met.

To accomplish this purpose of magnetic particle inspection, a light industrial oil known in the industry as an inspection oil can be used. This oil has an appropriate viscosity and the ability to wet the magnetizable part thoroughly. The inspection oil allows for better migration of the particles in the carrier to the defect. It also acts to wet out and disperse the magnetic inspection particles. Furthermore, oil acts as a rust inhibitor, which is very important on all machined and finished parts—especially those parts made of iron or steel.

Yet oil being used as the liquid carrier also has a number of disadvantages. First, the oil is combustible or flammable. If the oil does burn, a great health hazard is created. The mere use of such a combustible ingredient consitutes a fire hazard to both life and property.

For the testing of critical machined parts such as those found in automotive and aircraft components, an oil medium is known to be useful due to the fact that an oily film provides some corrosion protection for the parts. However, one of the problems in using oil is, that in the case of pressing railroad wheels onto the highly machined axles, the oil tends to trap abrasive dust which interferred with the pressing operation.

Much more is known about oil as the carrier medium. This information does not take into account the importance of viscosity to surface coverage and particle migration. Viscosity has a great effect on magnetic inspection particles.

Furthermore, an individual working with the oil can suffer from dermatitis and exposure to fumes. These problems are further compounded by hazards inherent in the disposing of the used oil in an environmentally safe manner after such use. It is clear that such disposal problems complicate the use of an oil-based magnetic particle inspection system.

With all these problems found in the use of oil, it thus becomes desirable to find another appropriate liquid medium. One liquid lacking the fire hazard, dermatitis, fume and disposal problems is water. However, water can cause oxidation on the surface of the article being tested. Furthermore, water does not properly coat the surface of the article, nor does it permit proper dispersion of the magnetic inspection particles.

Wetting agents reduce the surface tension of water allowing it to wet out the magnetic inspection particles—as well as flow over and wet out the surface of the part being tested. They control the pH usually by the addition of borax and discourage corrosion by incorporating sodium nitrite.

Use of sodium nitrite has been regulated by United States Environmental Protection Agency. So other corrosion preventative mixtures are now in use as substitutes therefor. These substitute materials do not afford surface corrosion protection of the of the ferrous surface.

If environmentally safe components can be added to water to improve wettability and corrosion resistance, if is possible for water to be used as the carrying liquid for magnetic inspection particles. Its use as a liquid carrier can be further enhanced, if the viscosity can be adjusted to achieve the desired results in the migration of the magnetic inspection particles.

It thus becomes clear that it is highly desirable to develop a conditioned, water-based carrier to be used as an inspection medium in the wet method of magnetic particle inspection.

SUMMARY OF THE INVENTION

Therefore, it is an objective of this invention to provide a water based carrier for magnetic particles to be used in a magnetic particle inspection system.

A further objective of this invention is to provide a testing system to test an article before it is placed in use.

A still further objective of this invention is to provide a testing system for an article to find flaws not readily visible to the human eye.

Yet a further objective of this invention is to provide a testing system for an article which avoids destruction of the article.

Also an objective of this invention is to provide a testing system for an article which minimizes use of statistics.

Another objective of this invention is to provide a testing system for a steel article.

Still another objective of this invention is to provide a testing system for an iron-containing article.

Yet another objective of this invention is to provide a testing system for a magnetizable article.

A further objective of this invention is to provide an improved liquid medium for magnetic particle inspection.

A still further objective of this invention is to provide a liquid medium for magnetic particle inspection having an appropriate viscosity.

Yet a further objective of this invention is to provide a liquid medium for magnetic particle inspection having an appropriate dispersing capability.

Also an objective of this invention is to provide a liquid medium for magnetic particle inspection having an appropriate capability of wetting the article to be tested.

Another objective of this invention is to provide a liquid medium for magnetic particle inspection having an appropriate capability for the particles to migrate to the surface of the article being tested.

Still another objective of this invention is to provide a magnetic particle inspection system which avoids the use of oil.

Yet another objective of this invention is to provide a liquid medium for magnetic particle inspection having an appropriate capability, which inhibits corrosion of the article being tested.

A further objective of this invention is to provide a non-combustible liquid medium for magnetic particle inspection.

A still further objective of this invention is to provide a liquid medium for magnetic particle inspection, which minimizes dermatitis.

Yet a further objective of this invention is to provide a liquid medium for magnetic particle inspection, which minimizes exposure to fumes.

Also an objective of this invention is to provide a liquid medium for magnetic particle inspection having minimized environmental hazards.

Another objective of this invention is to provide a water-based liquid medium for magnetic particle inspection having an appropriate capability for the particles to migrate to the surface of the article being tested.

Still another objective of this invention is to provide a magnetic particle inspection system which minimizes fumes.

Yet another objective of this invention is to provide a method, which tests an article before it is placed in use.

A further objective of this invention is to provide a method for testing an article to find flaws not readily visible to the human eye.

A still further objective of this invention is to provide a method for testing an article which avoids destruction of the article.

Also an objective of this invention is to provide a method for testing an article which minimizes use of statistics.

Another objective of this invention is to provide a method for testing a steel article.

Still another objective of this invention is to provide a method for testing an iron-containing article.

Yet another objective of this invention is to provide a method for testing a magnetizable article.

A further objective of this invention is to provide an improved liquid medium for magnetic particle inspection, which is readily disposable.

A still further objective of this invention is to provide an improved liquid medium for magnetic particle inspection, which minimizes or eliminates contamination of effluent from the testing plant.

These and other objectives (which other objectives become clear by considering the specification and claims as a whole) of this invention are met by providing a water based slurry of magnetic particles including a corrosion inhibitor, a surface tension adjusting agent, an antifoam agent, a viscosity adjustment element, and a buffering element.

DESCRIPTION OF THE PREFERRED EMBODIMENTS

A composition for use in a magnetic particle inspection system is formed by using water -- having therein a corrosion inhibitor, a surface tension reducing agent, an antifoam agent, a viscosity adjustment agent, and a buffering agent. This water-based composition can then be used as a suitable carrier for magnetic inspection particles. As this water-based composition is combined with magnetic inspection particles to form a slurry or suspension, the combination becomes a magnetic particle inspection system.

A magnetizable article may then be sprayed with, dipped into, or otherwise coated with the slurry. At a suitable point the article is magnetized. The resultant, magnetized article attracts the particles contained in the slurry. The particles are attracted to magnetic flux field variations of the article, the variations being caused by flaws in the article (if any).

The flaws in the article cause variations in the flux field of the article as magnetized. Each variation results in a small North-South magnetic polar set-up, which results in a buildup of magnetic inspection particles that is clearly visible under the appropriate light source.

Finally the article as thus treated is inspected under a suitable light source to determine any flaws which may be in the article. Typical light sources used are exemplified by, but not limited to ultra-violet, black light, sunlight, dichroic light, or other suitable light source.

The differing congregating points of the magnetic inspection particles indicate flaws or discontinuities in the article, and permit the article to be tested without destroying the article. The solution, as developed, covers the part like an oil and does not run off quickly from the surface of the article. It also provides a longer dwell time for the particles to orient on the flaw or discontinuity, without inhibiting the mobility of the particles to a defect.

COMPOSITION COMPONENTS

In the composition are ingredients including—about twenty-eight (28%) percent to about ninety-two (92%) percent water, about two (2%) percent to about seventeen (17%) percent by weight corrosion inhibitor, about one-half (0.5%) percent to about four (4%) percent surface tension reducing agent, about one (1%) percent to about eight (8%) percent antifoam agent, about two and one-half (2.5%) percent to about twenty-eight (28%) percent viscosity adjustment agent, and about two (2%) percent to about fifteen (15%) percent buffering agent.

More preferably, the composition includes about sixty (60%) percent to about ninety (90%) percent water, about two (2%) percent to about ten (10%) percent by weight corrosion inhibitor, about one-half (0.5%) percent to about three (3%) percent surface tension reducing agent, about one (1%) percent to about five (5%) percent antifoam agent, about three (3%) percent to about fifteen (15%) percent viscosity adjustment agent, and about two (2%) percent to about ten (10%) percent buffering agent.

Most preferably, the composition includes about eighty (80%) percent to about ninety (90%) percent water, about two (2%) percent to about five (5%) percent by weight corrosion inhibitor, about one-half (0.5%) percent to about two (2%) percent surface tension reducing agent, about one (1%) percent to about two (2%) percent antifoam agent, about four (4%) percent to about eight (8%) percent viscosity adjustment agent, and about two (2%) percent to about five (5%) percent buffering agent.

Into this water-based composition is placed up to about five (5%) percent by weight of the composition of fluorescent magnetic inspection particles. More preferably about 0.01 percent to about four (4%) percent by weight are used. Most preferably about 0.05 percent to about one (1%) percent by weight are used.

The fluorescent magnetic inspection particles may be replaced by non-fluorescent magnetic inspection particles. If non-fluorescent magnetic inspection particles are used, 0.05 to about four (4%) percent by weight of the composition of the fluorescent magnetic inspection particles. More preferably about 0.5 (%) percent to about 2.5 (%) percent by weight are used. Most preferably about 0.7 (%) percent to about 2.4 (%) percent by weight are used.

In this fashion, the corrosion, surface tension, and the viscosity of the composition can be controlled. These are the most important factors in any magnetic particle inspection system. Once these factors are controlled, the inspection can begin.

COMPOSITION PARAMETERS

To test whether the composition properly suspends the magnetic inspection particles and does not interfere with an accurate knowledge of the amount of particles present, a portion of the slurry containing the magnetic inspection particles is placed into a 100 milliliter pear-shaped centrifuge tube. The volume of particles settling into the stem of the tube determines whether the particles are properly suspended. An appropriate result of the settling test for florescent magnetic inspection particles is about 0.1 to about 0.5 milliliters at a time of thirty minutes. This is in accordance with military specification MIL-I-6868 E. For the non-fluorescent particles, the amount is about 1.0 to about 2.4 milliliters at a time of thirty minutes.

When working with fluorescent magnetic inspection particles, it is essential that the solution used as the carrier be free of fluorescence from any of its components. A requirement of many industry standards, an inspection media may not contain any fluorescent hue as this will interfere with the proper interpretation of the actual fluorescent magnetic particles reading on the part.

Another source for a settling bulb test is defined in AMS 3044B, which is a standard testing specification for the solution. This test suspension is placed in the pear-shaped centrifuge tube. After a period of time, the volume of particles settling out determines whether the solution is suitable for use or not.

CORROSION INHIBITOR

Typical of the corrosion inhibitors suitable for use is a polyamine borate inhibitor. Exemplifying the polyamine borates available is Monacor BE manufactured by Mona Industries Incorporated of Paterson, New Jersey. The Monacor BE appears as a clear, viscous liquid has a specific gravity at 25° centigrade of 1.107, a density of 9.24 pounds per gallon or 1.11 kilograms per liter, and a pH in a one (1%) percent concentration of 9.1.

Another suitable corrosion inhibitor is disodium 2,5,-dimercaptothiadiazole. This composition is available from the R. T. Vanderbilt Company of Norwalk, CT. This corrosion inhibitor has a color of light amber to brown, is clear; and has a slight odor, a density of 1.30 milligrams per cubic meter, an Assay value of 40.2% and a pH of 8.9. The disodium 2,5, -dimercaptothiadiazole is available from R. T. Vanderbilt, Inc., under the United States Patent and Trademark Office Registered Trademark of Vanchem NATD.

Another suitable corrosion inhibitor is also available from R. T. Vanderbilt Company, Inc. This inhibitor is sodium mercaptobenzothiazole—having a density of 1.255 milligrams per cubic meter, and a clear amber color. Its clarity indicates freedom from all suspended matter. It has about five percent maximum free alkalinity expressed as NaOH. It is soluble in water, alcohols, and glycose. It is relatively nontoxic and nonirritating in dilute solutions.

Also suitable for use is the triethanolamine salt of dimercaptothiadiazole. This compound appears as a liquid, light yellow in color, having a density of 1.16 milligrams per cubic meter, and a pH of 7.5 to 9.5.

Among all of the corrosion inhibitors, the polyamine borate is the most effective. This polyamine borate inhibitor is usable throughout the range of magnetizable articles, which may be tested by the magnetic particle inspection. Other inhibitors are useful only for certain articles. Any suitable branched or straight chain polyamine borate may be used as the corrosion inhibitor. Specific examples of the groups used with the polyamine borate are linear alkenyl, linear and branched alkyl, aryl, xylene, naphthalene, linear or branched alkyl benzene, decyl, lauryl, cetyl stearyl and mixtures thereof.

The polyamine borate inhibitor is preferred because of its effective use on all types of irons and steels. The other inhibitors are applicable to certain types of steel. The polyamine borates are the most effective corrosion inhibitors for a wide variety of surfaces. Corrosion is an inherent problem in testing with the magnetic particle inspection system. Many different types of steel, iron, and other magnetizable surfaces are encountered in magnetic particle inspection. It is for these reasons that the effective use of polyamine borates on all of these surfaces makes the polyamine borates the most efficient corrosion inhibitor for the purposes of magnetic particle inspection as seet forth in this invention.

SURFACE TENSION REDUCING AGENT

Any suitable surfactant can be used in the composition of this invention to serve as a surface tension reducing agent and to achieve the desired surface tension adjustment. The surfactant is needed to put the magnetic inspection particles in solution and keep them suspended there. This reduction of the surface tension also allows proper wetting of the surface of the part being tested.

The inherent surface tension of water interferes with the dispersion of the testing particles through the liquid. It is required to add a surfactant to reduce that surface tension. A number of well-known surfactants and combinations thereof are suitable for use in this testing medium.

The preferred surfactant is a combination of sodium dioctyl sulfosuccinate and sodium benzoate. This surfactant is available from Mona Industries, Incorporated of Paterson, New Jersey under the trade name of Monawet (MO-85P). Monawet (MO-85P) appears as a fine white powder having an activity 85.0 (%) percent with a 15 (%) percent sodium benzoate diluent. It is 0.85 (%) percent soluble in water at room temperature and has a pH of 6.5 at one (1%) percent concentration.

Another surfactant suitable for use is sodium dioctyl sulfosuccinate. This surfactant is available from the American Cyanamid Company of Greenwich, CT. The Tradename used by the American Cyanamid Company for this compound is Aerosol OT-B. The particular form is the Aerosol OT-B, which is a white granular solid containing solids of eighty-five (85) percent by weight, a specific gravity of 1.11 grams per centimeter, a melting point of about 300° Centigrade, an acid number of about 2.5, and an iodine value of 0.25. It is insoluble in organic polar solvents and soluble in organic nonpolar solvents.

Typical of the other surfactants that may be used are the sulfonates, sulfonic acid, alkylsulfate, alkylether sulfate, nonionic surfactants, anionic surfactants, and blends thereof. Cationic surfactants are excluded, but some amphoteric wetting agents can be used. Specific examples of the sulfonates are linear alkenyl, linear and branched alkyl, aryl, xylene, naphthalene, polymers. The sulfonic acid may be linear or branched alkyl benzene. The alkyl sulfate is generally selected from the group of decyl, lauryl, and cetyl stearyl. The alkylether sulfate is generally selected from the group consisting of alkylphenol, lauryl, or alkylpolyether. The nonionic surfactants are nonyl, phenol, lauryl, and ethylene oxide. Other surfactants that are suitable for use are the lauryl sulfo acetate, alkylolamids, and alphasulfo methyl esters.

It is desired to reduce the normal surface tension of water at about 70 dynes to a surface tension in the range of ten (10) to sixty (60) dynes. More preferably, the surface tension is reduced to 15 to 50 dynes. Most preferably, the surface tension is reduced to below 30 dynes.

Required also of the surface tension reducing agent is that the agent meet certain specifications—especially in that the dispersion of the particles passes the settling bulb test. The settling bulb test for compositions used in magnetic particle inspection is clearly defined in the military specifications MIL-I-6868E and AMS3044B.

ANTI-FOAMING AGENT

Almost any suitable antifoaming agent can be used. Most preferred of the antifoaming agents is the silicone emulsion available from Dow Corning of Midland, Michigan, under the name of Dow Corning DB31. The specific properties of this agent is that it is a silicone emulsion, having a white color with a specific gravity at 25° C. Centigrade of 1. The consistency is that of a creamy liquid. The pH is in the range of 4 to 5.

The antifoaming agent is essential in that foam can both trap the magnetic inspection particles and distort the defects in the article being tested. If the particles are held up in the foam, they are kept out of suspension in the slurry and cannot migrate to the defects or discontinuties in the article. If the particles have already migrated to the surface of the article, foam flowing over the article can distort the indications.

VISCOSITY ADJUSTMENT AGENT

Adjusting the viscosity is a very critical and necessary requirement of this composition. Proper surface coverage of the article must be similar to that which can be obtained using an inspection oil. Without the proper viscosity, the particles do not migrate properly to the surface of the article. A viscosity adjusting agent is required if water is to be used as the liquid medium. There are many products available which provide proper change in viscosity and give the required particle mobility.

The phosphate esters and sulfate esters fulfill the settling bulb requirements while providing the appropriate viscosity factors. Accordingly, these are the preferred materials for use as a viscosity adjusting agent.

The preferred anionic phosphorate suitable for use as a viscosity adjusting agent is available from Mona Industries Incorporated of Paterson, New Jersey under the trade name of Monafax 1214. Monafax 1214 has a surface tension of 31 dynes per centimeter and a drays wetting time of about 25. Its apperance is that of a clear viscous liquid, has a color under the GVCS33 system of 6, an activity of 100%, a pH of 2 in a 10% solution, a specific gravity of 25° of 1.22, acid value of a pH 5 of 238, an acid value at a pH of 9.8 at 427.

The most preferred viscosity adjusting agent is the sodium fatty alchol ether sulfate. It contains an alcohol solvent of thirty-five (35%) percent to forty (40%) percent by weight, has a boiling point of about 90° Centigrade, is combustible, and has a flash point of about 28° Centigrade. This product is available from Stephen Chemical Company, in Northfield, Illinois under the trade name of Steol CS-460. The weight of the compound is about 1 kilogram per liter.

Other suitable and appropriate viscosity adjusting agents are the anionic phosphorate of ethoxylated alcohol, and the ethoxylated alcohol sulfates. With these compounds or mixtures thereof, the viscosity can be adjusted as desired.

Still other suitable viscosity adjusting agents are the hydrophilic colloids. Typical colloids include polyacrylic acid, polyacrylamid, carboxy cellulose, starch, dextrin, and natural gums.

The standard viscosity of water is 1.0 centipoise—in relation to an average viscosity of 1.6 centipoise for an inspection oil. This use of viscosity adjusting agents permits the adjustment of the composition viscosity to the range of 1.3 to 3.0 centipoise—which is especially desired. This is attributable to the wide range of the effective viscosity. For example, evaporation of water from the system must be substantial before it can adversely effect the system. This range allows for the best possible surface coverage of a wide variety of articles.

Required also of the viscosity adjusting agent is that the agent meet certain specifications—especially in that the dispersion of the particles passes the settling bulb test. The setting bulb test for compositions used in magnetic particle inspection is clearly defined in the military specifications MIL-I-6868E and AMS3044B.

BUFFERING AGENT

The requirement of a buffering agent is best met by a boric acid buffering system. The boric acid buffer most effectively maintains the required pH range. Boric acid is also very easy to use. However, another acid buffer capable of keeping the pH below 9.2 is operable.

The buffer is necessary to keep the pH in the desired range. It is especially desirable that the pH be at least 7. If the pH becomes acidic (goes below 7), corrosion can occur. Thus, it is important to keep the pH above 7. It has been found that an especially useful pH is in the range of 7 to 10. More particularly, an especially useful pH is 7.5 to 9.2. The maximum 9.2 pH is set forth in military specification MIL-I-6868E. This pH range is preferred to be held in position by a boric acid buffer.

Selecting the ranges of these various agents and combining them results in a solution which when added to water creates a medium having corrosion resistance, reduced surface tension, and appropriate viscosity to achieve the desired results of testing the metal part.

The following examples are intended to illustrate without unduly limiting the invention. All parts and percentages are defined by weight of the total composition unless otherwise specified.

EXAMPLE 1

A cast steel gear is to be tested. Magnetic inspection particles are dispersed in an inspection oil (EXSOL D-80 available from the Exxon Corporation of New Jersey). The gear is sprayed with the slurry of oil and flourescent magnetic inspection particles, and subjected to a magnetic force. The magnetic inspection particles dispersed in the inspection oil migrate to the defects on the gear as the magnetic force is applied. Examination of the gear under black light during and after the application of the magnetic force shows that the gear is wetted by the oil, and the magnetic inspection particles migrate to the defects in the gear—indicating a minor crack in a tooth of the gear sufficient to result in the discard of the gear. The crack is not visible to the human eye.

EXAMPLE 2

The same gear as used in Example 1 is tested after it has been cleaned of the oil in a standard fashion. A composition is formed of 88.8% water, 2.8% polyamine borate as a corrosion inhibitor (available under the tradename Monacor BE, from Mona Industries, Paterson, N.J, 0.5% sodium dioctyl sulfosuccinate-sodium benzoate as a surfactant (available under the tradename Monawet MO-85P, from Mona Industries ), 1.0% silicone anti-foaming agent (available under the tradename Dow Corning DB 31, from Dow Corning, Midland, Mi, 2.3% boric acid as a buffering agent, and 4.6% anionic phosphate ester as a viscosity adjusting agent (available under the tradename Monafax 1214 from Mona Industries of Paterson, N.J. Into the composition is slurred 0.1% magnetic inspection particles by weight of the composition.

The gear is sprayed with the slurry and subjected to a magnetic force. The magnetic inspection particles dispersed in the composition migrate to the defects on the gear as the magnetic force is applied. Examination of the defects on the gear under black light shows that the gear is wetted by the composition and the magnetic inspection particles adhere to the defects on the gear—indicating a minor crack in a tooth of the gear sufficient to result in the discard of the gear. These results are the same as in Example 1. The gear shows no additional corrosion as a result of the treatment.

EXAMPLE 3

The procedure of Example 2 is repeated, except that the composition is as follows: 88.2% water, 2.9% polyamine borate as a corrosion inhibitor (available under the tradename Monacor BE, from Mona Industries, Paterson, N.J., 0.5% sodium dioctyl sulfosuccinate-sodium benzoate as a surfactant (available under the tradename Monawet MO-85P, from Mona Industries), 1.0% silicone anti-foaming agent (available under the tradename Dow Corning DB 31, from Dow Corning, Midland, Mich., 2.5% boric acid as a buffering agent, and 4.9% sodium fatty alcohol ether sulfate as a viscosity adjusting agent (available under the tradename Steol CS-460 from Stepan Chemical Company of Northfield, Illinois). Into the composition is slurried 0.1% magnetic inspection particles by weight of the composition.

The results are the same as in Example 2.

EXAMPLE 4

The procedure of Example 2 is repeated, except that the composition is as follows: 89.3% water, 2.8% polyamine borate as a corrosion inhibitor (available under the tradename Monacor BE, from Mona Industries, Paterson, N.J., 2% sodium dioctyl sulfosuccinate-sodium benzoate as a surfactant (available under the tradename Monawet MO-85P, from Mona Industries), 1% silicone anti-foaming agent (available under the tradename Dow Corning DB 31, from Dow Corning, Midland, MI), 2.4% boric acid as a buffering agent, and 2.5% starch as a viscosity adjusting agent (available under the tradename Sta-Lok 400 from A. E. Staley Manufacturing Company of Decatur, Ill). Into the composition is slurried 0.1% magnetic inspection particles by weight of the composition.

The results are the same as in Example 2- except a settling bulb reading cannot be attained.

EXAMPLE 5

The procedure of Example 2 is repeated, except that the gear is made of cast iron. The results are the same. The treatment is enhanced by a lack of corrosion.

EXAMPLE 6

The procedure of Example 5 is repeated, except that the polyamine borate is replaced by disodium 2,5-dimercaptothiadiazole. Corrosion is noted.

EXAMPLE 7

The procedure of Example 6 is repeated, except that the gear is made of stainless steel. Corrosion is notably absent.

Because of the disclosure herein and solely because of the disclosure herein, certain modifications of the testing system disclosed herein can become clear to a person having ordinary skill in this art. Such modifications are clearly covered hereby.

What is claimed and sought to be secured by Letters Patent of the United States, is:

1. An aqueous testing system for determining a flaw in an article, wherein said system includes a water based slurry of magnetic particles, and said system further includes a corrosion inhibitor, a surface tension adjusting agent, an antifoam agent, a viscosity adjusting agent, and a buffering agent to assist in the corrosion resistance.

2. The aqueous testing system of claim 1, wherein said testing system comprises:
   a. about twenty-eight percent to about ninety-two percent by weight water;
   b. about two percent to about seventeen percent by weight corrosion inhibitor;
   c. about one-half percent to about four percent surface tension reducing agent;
   d. about one percent to about eight percent antifoam agent;
   e. about two and one-half percent to about twenty-eight percent viscosity adjustment agent; and
   f. about two percent to about fifteen percent buffering agent.

3. The aqueous testing system of claim 2, wherein said testing system comprises:
   a. about sixty percent to about ninety percent by weight water;
   b. about two percent to about ten percent by weight corrosion inhibitor;
   c. about one-half percent to about three percent surface tension reducing agent;
   d. about one percent to about five percent antifoam agent;
   e. about three percent to about fifteen percent viscosity adjustment agent; and
   f. about two percent to about ten percent buffering agent.

4. The aqueous testing system of claim 3, wherein said testing system comprises:
   a. about eighty percent to about ninety percent by weight water;
   b. about two percent to about five percent by weight corrosion inhibitor;
   c. about one-half percent to about two percent surface tension reducing agent;
   d. about one percent to about two percent antifoam agent;
   e. about four percent to about eight percent viscosity adjustment agent; and
   f. about two percent to about five percent buffering agent.

5. The aqueous testing system of claim 2, wherein said testing system further comprises up to about five (5%) percent fluorescent magnetic inspection particles by weight of said system.

6. The aqueous testing system of claim 5, wherein said testing system further comprises about 0.05 to about 0.2 percent of said fluorescent magnetic inspection particles by weight of said system.

7. The aqueous testing system of claim 5, wherein:
   a. said corrosion inhibitor is at least one compound selected from the group consisting of polyamine borate; disodium 2,5,-dimercaptothiadiazole, sodium mercaptobenzothiazole, and triethanolamine salt of dimercaptothiadiazole;
   b. said surface tension reducing agent is at least one surfactant selected from the group consisting of sodium dioctyl sulfosuccinate, a sulfonate, a sulfonic acid, an alkylsulfate, and alkylether sulfate, a nonionic surfactant, and an anionic surfactant;
   c. said antifoaming agent is a silicone emulsion;
   d. said viscosity adjustment agent is at least one compound selected from the group consisting of a phosphate ester and a sulfate ester;
   e. said buffering agent is a boric acid based buffering agent.

8. The aqueous testing system of claim 6, wherein said viscosity adjustment agent is at least one compound selected from the group consisting of a polyacrylic acid, a polyacrylamid, carboxy cellulose, starch, dextrin, and natural gums.

9. The aqueous testing system of claim 8, wherein said viscosity adjustment agent is at least one selected from the group consisting of a phosphate ester and a sulfate ester.

10. The aqueous testing system of claim 9, wherein said system has a pH of at least 7.

11. The aqueous testing system of claim 10, wherein said system has a pH in the range of at least 7.5 to 9.2.

12. The aqueous testing system of claim 9, wherein said polyamine borate inhibitor includes at least one component selected from the group consisting of linear alkenyl, linear and branched alkyl, aryl, xylene, napthalene, linear alkyl benzene, branched alkyl benzene, decyl, lauryl, and cetyl stearyl.

13. The aqueous testing system of claim 10, wherein said surfactant is at least one component selected from the group consisting of a sulfonate, and alkyl sulfate, a sulfonic acid and an alkyl ether sulfate.

14. The aqueous testing system of claim 13, wherein:
   a. said sulfonate is at least one sulfonate selected from the group consisting of a linear alkenyl, linear and branched alkyl, aryl, xylene, and naphthalene;
   b. said sulfonic acid is at least one sulfonic acid selected from the group consisting of a linear alkyl benzene and a branched alkyl benzene;
   c. said alkyl sulfate is at least one alkyl sulfate selected from the group of decyl, lauryl, and cetyl; and
   d. said alkylether sulfate is generally selected from the group consisting of alkylphenol, lauryl, and alkylpolyether.

15. The aqueous testing system of claim 10, wherein said nonionic surfactant is at least one component selected from the group consisting of a nonyl, phenol, lauryl, and ethylene oxide.

16. The aqueous testing system of claim 15, wherein said system has a surface tension of ten dynes to sixty dynes.

17. The aqueous testing system of claim 16, wherein said system has a surface tension below thirty dynes.

18. The aqueous testing system of claim 17, wherein said system has a viscosity range of 1.3 to 3.0 centipoise.

19. The aqueous testing system of claim 8, wherein said viscosity adjustment agent is at least one selected from the group consisting of an ethoxylated lauryl alcohol sulfate and an ethoxylated lauryl alcohol phosphate to increase the solution viscosity to between 1.3 centipoises and 3.0 centipoises;

20. The aqueous testing system of claim 2, wherein said testing system further comprises about 0.09 to about 2.4 percent of non-fluorescent magnetic inspection particles by weight of said system.

* * * * *